(12) United States Patent
Olalde Rangel

(10) Patent No.: US 7,604,823 B2
(45) Date of Patent: Oct. 20, 2009

(54) SYNERGISTIC HIV/AIDS AND/OR IMMUNE DISEASE PHYTO-NUTRACEUTICAL COMPOSITION

(75) Inventor: Jose Angel Olalde Rangel, 519 Cleveland St., Suite 101, Clearwater, FL (US) 33755

(73) Assignee: Jose Angel Olalde Rangel, Clearwater, FL (US)

( * ) Notice: Subject to any disclaimer, the term of this patent is extended or adjusted under 35 U.S.C. 154(b) by 0 days.

(21) Appl. No.: 11/470,842

(22) Filed: Sep. 7, 2006

(65) Prior Publication Data

US 2008/0063658 A1    Mar. 13, 2008

(51) Int. Cl.
*A61K 36/254* (2006.01)
*A61K 36/28* (2006.01)
*A61K 36/33* (2006.01)

(52) U.S. Cl. .................. 424/728; 424/737; 424/767

(58) Field of Classification Search ........................ None
See application file for complete search history.

(56) References Cited

U.S. PATENT DOCUMENTS

| | | | | |
|---|---|---|---|---|
| 5,770,217 | A * | 6/1998 | Kutilek et al. | 424/442 |
| 6,805,866 | B2 * | 10/2004 | Keith et al. | 424/195.15 |
| 7,070,813 | B2 * | 7/2006 | Jensen et al. | 424/725 |
| 2005/0002962 | A1 * | 1/2005 | Pasco et al. | 424/195.15 |

FOREIGN PATENT DOCUMENTS

| | | | |
|---|---|---|---|
| KR | 2003082619 | * | 10/2003 |
| KR | 2004085226 | * | 10/2004 |
| RU | 2241478 | * | 12/2004 |
| WO | WO 01/34170 | * | 5/2001 |

OTHER PUBLICATIONS

Phytobiotic Immune Support Formula. Retrieved from the Internet. May 23, 2003. <http://web.archive.org/web/20030523173124/http://www.yourvitalhealth.com/products/prod-phytobiotic.cfm>. Retrieved on Oct. 8, 2008.*
Sutherlandi Dot Org. Retrieved from the internet. Oct. 19, 2001. <http://web.archive.org/web/20011019223144/http://www.sutherlandia.org/> Retrieved on Oct. 8, 2008.*
Suma. Retrieved from the internet. Jan. 20, 1998. <http://web.archive.org/web/19980120171321/http://www.rain-tree.com/suma.htm> Retrieved on Dec. 9, 2008.*
Shark Cartilage. Retrieved from the internet. Aug. 12, 2002. <http://web.archive.org/web/20020812130238/http://www.enerex.ca/articles/shark_catilage.htm> Retrieved on Oct. 9, 2008.*
Immune Mix. Retrieved from the internet. Aug. 27, 2002. <http://web.archive.org/web/20020827133232/http://www.natural-remedies-hiv-aids.com/immune_mix2.htm> Retrieved on Otcober 9, 2008.*
Williams et al. Selected Secondary Metabolites From the Phytoaccaceae and Thir Biological/Pharmaceutical Significance. Recent Developments in Phytochemistry. 2002. 6. Abstract.*

* cited by examiner

*Primary Examiner*—Patricia Leith
*Assistant Examiner*—Melenie McCormick

(57) ABSTRACT

Phytoceutical composition for the prevention and treatment of HIV/AIDS and/or immune disorders. A specific combination of extracts of plants is taught, as well as the formulations based on categorizing plants into one of three groups, Energy, Bio-Intelligence and Organization. Such combination has synergistic effects, with minimal side effects.

1 Claim, No Drawings

SYNERGISTIC HIV/AIDS AND/OR IMMUNE DISEASE PHYTO-NUTRACEUTICAL COMPOSITION

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a phytoceutical formulation used to treat HIV/AIDS and/or immune related diseases. The formulation is a particular combination of plants and has a synergistic effect in combination.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process.

As pointed out by Tyler (1999), this synergistic or additive pharmacological effect can be beneficial by eliminating the problematic side effects associated with the predominance of a single xenobiotic compound in the body. In this respect, Kaufman et al. (1999) extensively documented how synergistic interactions underlie the effectiveness of a number of phytomedicines. A more recent study with additional demonstration concerning a phytomedicine's synergistic effect—Echinacea—is provided by Dalby-Brown et al, 2005. This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses (Kaufman et al., 1999; Wink, 1999). Conclusion: On one hand, synthetics may have the required efficacy for disease treatments; however this can be marred by severe side effects. On the other hand, despite the excellent medicinal qualities of many plants, they are individually insufficient to take chronic degenerative diseases into remission. However, there is mounting evidence which demonstrate that medical plants contain synergistic and/or side-effect neutralizing combinations (Gilani and Rahman, 2005). Thus, what are needed in the art are better treatment regimes with improved patient tolerance, while providing sufficient efficacy.

SUMMARY OF THE INVENTION

A number of known beneficial plants were classified according to their capacity to enhance the three main elements that support overall health, in chronic degenerative diseases: Energy (E), Bio-intelligence (I) and Organization (O). A synergistic effect is expected when all three categories of herbs (E, I, O) are included in a formulation.

Thus, on the case of diseases that cause a depression and/or attack to the immune system, one embodiment of the invention provides an effective, natural composition for treating the aforementioned diseases. The composition can be used alone, or can be combined with simultaneous use of one or more pharmaceutical compositions. It can be used for the treatment of HIV/AIDS, immune disorders and others.

DETAILED DESCRIPTION OF THE INVENTION

'Pharmaceutically acceptable excipients' is used herein according to art accepted meanings, and includes those ingredients needed to formulate a medicine for mammalian use, including the use of gelatin capsules.

'Synergistic' or 'synergy' is used herein to mean that the effect is more than its additive property. In preferred embodiments, the synergy is at least 1.5, 2, 5, or 10 fold.

By use of 'plants,' what is meant herein is that the plant (or that portion with medicinal activity) is used whole, ground, or as an extract. Also included are purified active ingredients, and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only, and should not serve to unduly limit the invention.

EXAMPLE 1

Plant Characteristics—HIV/AIDS and Immune Disorders

Energy Enhancing Components.—

*Eleutherococcus* or *Acanthopanax senticosus* (Russian Ginseng, Siberian Ginseng, Eleuthero, Devil's Shrub, Buisson du Diable, Touch-me-not, Wild Pepper, Shigoka, *Acantopanacis senticosus*). Contains terpenoids (oleanolic acid), Eleutheroside A (daucosterol); Eleutheroside B (siringin); Eleutheroside B1 (isofraxidin); Eleutheroside B4 (sesamin); Eleutheroside D and E (heteroside siringoresinol); Eleutheroside C, G, I, K, L and M; phytosterols (β-sitosterol), polysaccharides (eleutherans), volatile oils, caffeic acid, coniferyl aldehyde, and sugars.

*Eleutherococcus*, increases energy and vitality levels, improving physical and mental performance, and quality of life. It increases the contribution of oxygen to muscles and allows for longer exercising and faster recovery. Prevents tiredness: the adaptogenic effects of the root of *eleutherococcus* are produced by metabolic regulation of energy, nucleic acids, and tissular proteins. Eleuthero improves the formation of glucose-6-phosphate. The glucose-6-phosphate oxidizes by the way of pentose, producing substrates for the biosynthesis of nucleic acids and proteins. On the other hand, it increases the activity of succinate dehydrogenase and of muscular malate-dehydrogenase, enzymes that intervene in the cycle of tricarboxilic acids, generating ATP. The eleutherosides B and E are responsible for this adaptogenic activity. Eleuthero has been shown to bind to gluco or mineralocorticoid receptors and stimulate production of T-lymphocyte and natural killer cells (immune-stimulant activity). It has antioxidant activity as well as. Russian Ginseng contains at least 40 active ingredients.

*Panax ginseng* (Chinese ginseng, *panax*, ren shen, jintsam, ninjin, Asiatic ginseng, Japanese ginseng, Oriental ginseng, Korean red ginseng) The main active components are ginsenosides (protopanaxadiols and protopanaxatriols types) these have been shown to have a variety of beneficial effects, including immune modulator, anti-inflammatory, antioxidant, and anticancer effects. They also confer energizing properties because they increase ATP synthesis. Results of clinical research studies demonstrate that *Panax* may improve immune function. Studies indicate that *Panax* enhances phagocytosis, NK lymphocytes cell activity, and the production of interferon; improves physical and mental performance in mice and rats; and increases resistance to exogenous stress factors. A Clinical Trial on 68 HIV-1-infected patients who lived for more than 5 years without antiretroviral therapy showed that long-term intake of Korean red ginseng (KRG) delays disease progression in human immunodeficiency virus type 1 (HIV-1) infected patients; significantly slowed the decrease in CD4 T cells and significantly decreased CD8 antigen level (Sung H, Kang S M, Lee M S. Korean red ginseng slows depletion of CD4 T cells in HIV-1 infected patients. Clin Diagn Lab Immunol. 2005; 12:497-501). A xylanase isolated from the roots of *Panax ginseng* inhibits HIV-1 reverse transcriptase (Lam S K, Ng T B. A xylanase from roots of sanchi ginseng (Panax notoginseng) with inhibitory effects on human immunodeficiency virus-1 reverse transcriptase. Life Sci. 2002; 70:3049-58).

A Clinical controlled trial in 18 human immunodeficiency virus (HIV-1) infected patients showed that CD4+ T cell counts maintained or even increased for a prolonged period in patients treated only with Korean red ginseng. CD4+ T cell counts maintained in the ginseng+ZDV whereas the CD4+ T cell counts in patients treated only with ZDV decreased. Also, the development of resistance mutations in reverse transcriptase to zidovudine was delayed (Cho Y K, Sung H, Lee H J. Long-term intake of Korean red ginseng in HIV-1-infected patients: development of resistance mutation to zidovudine is delayed. Int Immunopharmacol. 2001; 1:1295-1305). Both echinacea and ginseng significantly enhanced NK-function of patients with either the chronic fatigue syndrome or the acquired immunodeficiency syndrome. Similarly, the addition of either herb significantly increased antibody-dependent cellular citotoxicity of peripheral blood mononuclear cells from all subject groups (See D M, Broumand N, Sahl L. In vitro effects of echinacea and ginseng on natural killer and antibody-dependent cell cytotoxicity in healthy subjects and chronic fatigue syndrome or acquired immunodeficiency syndrome patients. Immunopharmacology. 1997; 35:229-35). *P. ginseng* provides at least 86 active principles in a single therapeutic.

*Panax quinquefolius* (American Ginseng, Anchi, Canadian Ginseng, Five Fingers, Ginseng, American, North American Ginseng, Red Berry, Ren Shen, and Tienchi) Related to *Panax ginseng*, it's a distinct species with higher ginsenoside Rb1 levels and without ginsenoside Rf. Rb1 confers energizing properties because they increase ATP synthesis. It has immune modulator, antioxidant and anti-inflammatory effects. Extracts of *P. quinquefolius* root were found to significantly stimulate alveolar macrophage TNF release (Assinewe V A, Extractable polysaccharides of *Panax quinquefolius* L. root stimulates TNF-alpha production by alveolar macrophages. Phytomedicine. 2002; 9:398-404). Quinqueginsin, a homodimeric protein isolated from the roots of *Panax quinquefolius* possesses an inhibitory action expressed toward human immunodeficiency virus-1 reverse transcriptase (Wang H X, Ng T B. Quinqueginsin, a novel protein with anti-human immunodeficiency virus, antifungal, ribonuclease and cell-free translation-inhibitory activities from American ginseng roots. Biochem Biophys Res Commun. 2000; 269:203-8). *P. quinquefolius* provides at least 206 active principles in a single therapeutic.

*Pfaffia paniculata* (Suma, Brazilian Ginseng, *Pfaffia*, Para Tudo, Corango-acu, *Hebanthe paniculata, Gomphrena paniculata, G. eriantha, Iresine erianthos, I. paniculata, I. tenuis, P. eriantha, Xeraea paniculata*) contains active glycosides (beta-ecdysone and three ecdysteroids), six different pfaffic acids, phytosterols (sitosterol and stigmasterol) and triterpene glycosides. *Pfaffia* contains up to 11% Saponins (triterpene glycosides), which two derived products have received patents in Japan as antineoplasic compositions. Its germanium content probably accounts for its properties as an oxygenator at the cellular level, and its high iron content may account for its traditional use for anemia. This herb increases energy through an increase in ATP synthesis and oxygenation at the cellular level, and it also has anabolic activity at the muscular level. Incorporation of this phytomedicine provides at least 44 active principles in a single therapeutic.

*Rhodiola rosea* (Golden Root, Roseroot, Artic root) consists mainly of phenilpropanoids (rosavin, rosin, rosarin—all specific to *R. rosea*), phenylethanol derivatives (salidroside, rhodioloside, tyrosol), flavanoids (catechins, proanthocyanidins, rodiolin, rodionin, rodiosin, acetylrodalgin, tricin), monoterpenes (rosiridol, rosaridin), triterpenes (daucosterol, beta-sitosterol), and phenolic acids (chlorogenic, caffeic, hydroxycinnamic and gallic acid). There are many species of Rhodiola, but rosavins seem to be unique to R. Rosea, and it is the preferred species for this formulation. Rhodiola increases energy levels because it activates ATP synthesis and re-synthesis in mitochondria, stimulating reparative processes after intense exercise. Incorporation of this phytomedicine provides at least 28 active principles in a single therapeutic.

*Schizandra chinensis* (*Schisandra spenenthera*, Chinese magnolia vine fruit, also known as Wuweizi and Wurenchum). *Schizandra*'s major active principles are lignans called schizandrines. Schizandra increase activities in some enzymes that intervene in the oxidative phosphorylation. It reduces fatigue and increases exercise resistance. Gomisin J (a derivative of lignans compound) was found to be a potent inhibitor of the cytopathic effects of human immunodeficiency virus type 1 (HIV-1) on MT-4 human T cells. Gomisin J derivatives were active in preventing p24 production from acutely HIV-1-infected H9 cells. One of these derivatives was active against 3'-azido-3'-deoxythymidine-resistant HIV-1, acted synergistically with AZT and 2',3'-ddC and inhibited HIV-1 reverse transcriptase in vitro.

Schizandra also inhibited the early phase of the HIV life cycle (Fujihashi T, Hara H, Sakata T. Anti-human immunodeficiency virus (HIV) activities of halogenated gomisin J derivatives, new nonnucleoside inhibitors of HIV type 1 reverse transcriptase. Antimicrob Agents Chemother. 1995; 39:2000-7). Schisandra provides at least 81 active principles.

Bio-Intelligence Modulators.—

*Andrographis paniculata* (King of Bitters, Kalmegh, Quasabhuva, The Creat and Kirayat) Primary active principles associated with Andrographis (AG) are: flavonoids, glucosides and diterpenic lactones (andrographolides). As evidenced in various clinical studies, these substances offer immune-modulator and anti-inflammatory properties. Studies also suggest that they stimulate the immune systems and activate macrophages. A phase I dose-escalating clinical trial of andrographolide from *Andrographis* paniculata was conducted in 13 HIV positive patients and five HIV uninfected, healthy volunteers. No subjects used antiretroviral medications during the trial. A significant rise in the mean CD4(+) lymphocyte level of HIV subjects occurred after administration of andrographolide. Andrographolide may inhibit HIV-induced cell cycle dysregulation, leading to a rise in CD4(+) lymphocyte levels in HIV-1 infected individuals (Calabrese C, Berman S H, Babish J G. A phase I trial of andrographolide in HIV positive patients and normal volunteers. Phytother Res. 2000; 14:333-8). Dehydroandrographolide succinic acid monoester, by virtue of its protease inhibitory property, possibly acts by suppressing the proteolytic cleavage of envelope glycoprotein gp160 of HIV (Basak A, Cooper S, Roberge A G. Inhibition of proprotein convertases-1, -7 and furin by diterpines of Andrographis paniculata and their succinoyl esters. Biochem J. 1999; 338:107-13). This plant offers at least 11 active principles in a single therapeutic.

*Astragalus membranaceus* (Huang-Qi, Huangqi) This plant contains three main types of active principles. Isoflavones, which act as anti-oxidants; astragalans which act as immune-stimulants and anti-inflammatory by stimulating the phagocytic activity of macrophages, of the cytotoxic response of T and NK lymphocytes and of the production and activity of interferon; and astragalosides which act as modulators of the hypothalamus-hypofisis-adrenal axis response. It also conveys antioxidative properties.

The in vitro induction of LAK cell activity was studied in cancer and AIDS patients. F3, an immune-regulatory component of *Astragalus membranaceus* was shown capable of potentiating the LAK cell inducing activity of rIL-2. With F3 plus rIL-2, the effector to target cell ratio could be reduced to one-half in order to obtain an equivalent level of cytotoxicity when rIL-2 was used alone. In some patients, F3 could make them responsive to rIL-2. These results imply that F3 may be useful to potentiate LAK cell activity, reduce the amount of rIL-2 and thus minimize the latter's toxic side effects when used in vivo. (Chu D T, Lin J R, Wong W. The in vitro potentiation of LAK cell cytotoxicity in cancer and aids patients induced by F3—a fractionated extract of *Astragalus membranaceus*] Zhonghua Zhong Liu Za Zhi. 1994; 16:167-71). This plant offers at least 38 active principles in a single therapeutic.

*Coriolus versicolor* (Kawara take, Yun zhi, turkey tail) Among the active principles isolated from the mycelia of Chinese Medicinal fungus *Coriolus versicolor* is the polysaccharide peptide (PSP) which has proven its benefits in many clinical trials in China and Japan. Another active principle of *Coriolus* is protein bound polysaccharide Krestin (PSK). Polysaccharopeptide (PSP) isolated from the edible mushroom *Coriolus versicolor* demonstrated inhibition of the interaction between HIV-1 gp120 and immobilized CD4 receptor, potent inhibition of recombinant HIV-1 reverse transcriptase, and inhibited a glycohydrolase enzyme associated with viral glycosylation (Collins R A, Ng T B. Polysaccharopeptide from *Coriolus versicolor* has potential for use against human immunodeficiency virus type 1 infection. Life Sci. 1997; 60:PL383-7). The ability of polysaccharide PSK to inhibit four different strains of human immunodeficiency virus type 1 (HIV-1), a strain of type 2 (HIV-2), and a human T-cell lymphotropic virus type I (HTLV-1) was tested. Cell-free infection of HIV-1 and HIV-2 was almost completely blocked. Cell-to-cell infection by HIV-1, HIV-2, and HTLV-1 was also inhibited (Tochikura T S, Nakashima H, Yamamoto N. Antiviral agents with activity against human retroviruses. J Acquir Immune Defic Syndr. 1989; 2:441-7). PSK has an antiviral effect on human immunodeficiency virus (HIV) in vitro. One of the mechanisms of this effect is attributable to the inhibition of binding of HIV with lymphocytes. PSK inhibits reverse transcriptase in a non-competitive way.

PSK almost completely blocked the cytopathic effect such as giant cell formation and HIV-specific antigen expression both in MT-4 cells and MOLT-4 cells. Pretreatment of the virus with PSK may specifically interfere with early stages of HIV infection by modifying the viral receptor (Tochikura T S, Nakashima H, Hirose K. A biological response modifier, PSK, inhibits human immunodeficiency virus infection in vitro. Biochem Biophys Res Commun. 1987; 148:726-33).

*Echinacea* spp. (*E. angustifolia, E. purpurea*, Black Sampson, Purple Coneflower, Rudbeckia, Missouri Snakeroot, Red Sunflower) contains alkaloids (Isotussilagine, tussilagine), amides (echinacein, isobutylamides), carbohydrates (echinacin, polysaccharides (heteroxylan and arabinogalactan), inulin, fructose, glucose, pentose), glycosides (echinacoside), terpenoids (Germacrane), Cichoric acid, betaine, methyl-para-hydroxycinnamate, vanillin, phytosterols, and volatile oils. The rich content of polysaccharides and phytosterols in *Echinacea* are what make it a strong immune system stimulant. The sesquiterpene esters also have immune-stimulatory effects. Echinacin, a component of *Echinacea*, also has cortisone-like actions which can help control the inflammatory reactions. The human immunodeficiency virus (HIV) integrase (IN) must covalently join the viral cDNA into a host chromosome for productive HIV infection. 1-Chicoric acid (1-CA) is a potent inhibitor of IN in vitro, and inhibits integration and entry. Using recombinant HIV IN, steady-state kinetic analyses with 1-CA were consistent with a noncompetitive or irreversible mechanism of inhibition. These data demonstrate that 1-CA is a noncompetitive but reversible inhibitor of IN in vitro and of HIV integration in vivo. Both echinacea and ginseng significantly enhanced NK-function of patients with either the chronic fatigue syndrome or the acquired immunodeficiency syndrome. In vitro effects of echinacea and ginseng on natural killer and antibody-dependent cell cytotoxicity in healthy subjects and chronic fatigue syndrome or acquired immunodeficiency syndrome patients. Immunopharmacology. 1997; 35:229-35). Finally, synergistic antioxidant effects of *Echinacea* constituents were found when cichoric acid (major caffeic acid derivative in *E. purpurea*) or echinacoside (major caffeic acid derivative in *Echinacea pallida* and *Echinacea angustifolia*) were combined with a natural mixture of alkamides and/or water extract containing the high molecular weight compounds.

This contributes to the hypothesis that the physiologically beneficial effects of Echinacea are exerted by the multitude of constituents present in the preparations (Dalby-Brown L, et al. Synergistic antioxidative effects of alkamides, caffeic acid derivatives, and polysaccharide fractions from Echinacea purpurea on in vitro oxidation of human low-density lipoproteins. J Agric Food Chem. 2005; 53:9413-23). The incorporation of this phytomedicine into compositions provides at least 70 active principles in a single therapeutic.

Ganoderma lucidum (Reishi, also G. tsugae, G. valesiacum, G. oregonense, G. resinaceum, G. pfezfferi, G. oerstedli, and G. ahmadii) is an edible fungus containing bitter triterpenoids (ganoderic acid), β-D-glucan, coumarins, alkaloids and ergosterols. The main active principles of this mushroom are sterols and beta-proteoglucans which bestow antiinflammatory and immune-modulating properties, because they increase the phagocytotic capacity of macrophages, and increase the production—and lifetime—of CD4 lymphocytes as well. The polysaccharide component with a branched (1→6)-beta-D-glucan moiety of G. lucidum (PS-G) has been reported to exert activation of natural killer cells. Also data suggests that PS-G can effectively promote the activation and maturation of immature dendritic cells suggesting that PS-G may posses a potential in regulating immune responses. A protein demonstrating laccase activity and potent inhibitory activity towards human immunodeficiency virus (HIV)-1 reverse transcriptase was isolated from the medicinal mushroom Ganoderma lucidum (Wang H X, Ng T B. A laccase from the medicinal mushroom Ganoderma lucidum. Appl Microbiol Biotechnol. 2006 Apr. 25). A new highly oxygenated triterpene named ganoderic acid alpha has been isolated from a extract of Ganoderma lucidum together with twelve known compounds. Ganoderiol F and ganodermanontriol were found to be active as anti-HIV-1 agents, and ganoderic acid B, ganoderiol B, ganoderic acid C1, 3 beta-5 alpha-dihydroxy-6beta-methoxyergosta-7,22-diene, ganoderic acid alpha, ganoderic acid H and ganoderiol A were moderately active inhibitors against HIV-1 PR (el-Mekkawy S, Meselhy M R, Nakamura N. Anti-HIV-1 and anti-HIV-1-protease substances from Ganoderma lucidum. Phytochemistry. 1998; 49:1651-7) (Min B S, Nakamura N, Miyashiro H. Triterpenes from the spores of Ganoderma lucidum and their inhibitory activity against HIV-1 protease. Chem Pharm Bull (Tokyo). 1998; 46:1607-12).

Two new lanostane-type triterpenes, lucidumol A and ganoderic acid beta were isolated from Ganoderma lucidum, together with a new natural one as well as seven that were already known. Ganoderic acid beta, (24S)-lanosta-7,9(11)-diene-3 beta, 24,25-triol (called lucidumol B), ganodermanondiol, ganodermanontriol and ganolucidic acid A showed significant anti-human immunodeficiency virus (anti-HIV)-1 protease activity. Ganoderma contains at least 32 active principles.

Grifola frondosa (Maitake, Dancing Mushroom; also G. sordulenta, Polyporus umbellatus and Meripilus giganteus) contains the primary polysaccharide, β-D-glucan in the 1.3 and 1.6 forms. It also contains alpha glucan, lipids, phospholipids, and ergosterol. β-D-glucan is recognized as an effective immune-stimulator. This substance increases the activity of macrophages and other immunocompetent cells. The substance also improves the immunological efficiency of these cells by increasing production of cytokines IL-1, IL-2 and others. The final result is an increase of the defenses against HIV infection. Other infections and tumoral diseases. Also, D-Fraction, a polysaccharide extracted from maitake mushrooms (Grifola frondosa), has been reported to exhibit an antitumoral effect through activation of immunocompetent cells, including macrophages and T cells, with modulation of the balance between T-helper 1 and 2 cells. Study results suggest that D-Fraction can decrease the effective dosage in tumor-bearing mice by increasing the proliferation, differentiation, and activation of immunocompetent cells and thus provide a potential clinical benefit for patients with cancer. Use of Grifola has demonstrated to diminish side effects of chemotherapy in test conducted in animals. Maitake (Grifola frondosa) is the Japanese name for an edible medicinal mushroom. Maitake is increasingly being recognized as a potent source of polysaccharide compounds with dramatic health-promoting potential. The D-fraction, the MD-fraction, and other extracts, often in combination with whole maitake powder, have shown particular promise as immunemodulating agents, and as an adjunct to cancer and HIV therapy (Mayell M. Maitake extracts and their therapeutic potential. Altem Med Rev. 2001; 6:48-60). Grifola (maitake) mushrooms have various degrees of immunomodulatory, lipid-lowering, antitumoral, and other beneficial or therapeutic health effects without any significant toxicity. The incorporation of this phytomedicine provides at least 6 active ingredients for therapeutic use.

Hydrastis canadensis (golden seal, yellow root, turmeric root) contains mainly isoquinoline alkaloids (xanthopuccine, berberine, hidrastine, hidrastanine, beta-hydrastine, canadine and canadaline). These confer anti-inflammatory, bacteriostatic, and bactericidal, effects. In general, its antibacterial action is directed to microbes' metabolic inhibition, inhibition of the formation of enterotoxins, and inhibition of bacterial adhesion. Berberine inhibits activating protein 1 (AP-1), a key factor in transcription of the inflammation. It also exerts a significant inhibitory effect on lymphocyte transformation, so its anti-inflammatory action seems to be due to the inhibition of DNA synthesis in the activated lymphocytes or to the inhibition of the liberation of arachidonic acid from the phospholipids of the cellular membrane. It also has immunomodulating properties by increasing production of immunoglobulins G and M and stimulating the phagocytotic capacity of macrophages. A study showed that Berberine, inhibits HIV-1 reverse transcriptase by means of a complex mechanism that includes both enzyme-berberine and berberine-template interactions; the latter effect also results in RT inhibition (Gudima S O, Memelova L V, Borodulin V B. Kinetic analysis of interaction of human immunodeficiency virus reverse transcriptase with alkaloids. Mol Biol (Mosk). 1994; 28:1308-14). This plant provides at least 34 active principles for therapeutic use.

Lentinus edodes (Hua gu, Shiitake, Shiitake mushroom) Lentinan, obtained from the Shiitake mushroom is a β1-3, β1-6 δ-glucan. Glucan preparations are always heterogeneous in molecular weight but Lentinan is particularly big, in the order of 400.000-1.000.000 daltons. Studies also show that lentinan boosts the immune system. Thus, the active principles are mostly present as glucans of different glycoside links, such as (1→3), (1→6)-beta-glucans y (1→3)-alpha-glucans and as true heteroglicanes. They act as immune modulators due to the increase in concentration of humoral mediators, such as: TNF-α, gamma interferon, Interleukin-2, Interleukin-6, and the production of NO and activity of catalase, in macrophages and T lymphocytes. They also increase the citotoxicity of NK cells and macrophages. Another active principle obtained from Lentinus is AHCC (Active Hexose Correlated Compound). This compound offers immune-modulating and antineoplasic activity. To be noted are also an improvement in Lymphocyte and erythrocyte count, anemia and appetite. Lentin, a novel protein was isolated from the edible mushroom Lentinus edodes.

Lentin exerted an inhibitory activity on HIV-1 reverse transcriptase (Ngai P H, Ng T B. It also has inhibitory effects on activity of human immunodeficiency virus-1 reverse transcriptase and proliferation of leukemia cells. Life Sci. 2003; 73:3363-74). Lentinan, a beta 1→3 glucan isolated from

*Lentinus edodes* (Shiitake mushroom) has immune modulating properties. A two phase I/II placebo-controlled trials on 98 patients was conducted. In one study at the San Francisco General Hospital (SFGH), ten patients were each administered lentinan or placebo. In the second study at the Community Research Initiative in New York (CRI), two groups of 20 patients each were administered lentinan, and ten patients were administered placebo. This study confirms the good tolerability of lentinan observed in Japanese cancer patients. Patients in the study have shown a trend toward increases in CD4 cells and in some patients' neutrophil activity. Subsequent to this study, a trial of lentinan in combination with didanosine (ddI) showed a mean increase of CD4 cells/mm3, in contrast to a decrease in CD4 cells in patients on ddI alone (Gordon et al. 1995) (Gordon M, Bihari B, Goosby E. A placebo-controlled trial of the immune modulator, lentinan, in HIV-positive patients: a phase I/II trial. J Med. 1998; 29:305-30). Lentinan, an immune modulator isolated from *Lentinus edodes* in combination with didanosine (ddI) was evaluated in a controlled study in HIV positive patients with low CD4 levels. A control group received ddI only. A total of 107 patients were enrolled at three sites, and 88 patients started the ddI/lentinan phase. The combination caused significant increases in CD4 levels, whereas ddI alone was significant (Gordon M, Guralnik M, Kaneko Y. A phase II controlled study of a combination of the immune modulator, lentinan, with didanosine (ddI) in HIV patients with CD4 cells of 200-500/mm3. J Med. 1995; 26:193-207). Lentinan, a (1----3)-beta-D-glucan with (1----6)-beta-D-glucopyranoside branches and its related polysaccharides increase host resistance to various kinds of bacterial, viral and parasitic infections including AIDS. Lentinan appears to represent Host Defense Potentiators (HDPs), which can restore or augment the ability of responsiveness of the host to lymphocytokines or other intrinsic bioactive factors through maturation, differentiation or proliferation of the important cells for host defense mechanisms. HDPs such as lentinan are the most appropriate drugs to prevent the manifestation of AIDS symptoms in HIV carriers (Chihara G. Recent progress in immunopharmacology and therapeutic effects of polysaccharides. Dev Biol Stand. 1992; 77:191-7).

*Morinda citrifolia* (Noni, Indian Mulberry, Ba Ji Tian, Nono, Nonu, Fruta de Queso and Nhau) A large range of its components have been identified. Noni encompasses at least 23 active principles, 5 vitamins and 3 minerals. Among them: several acids, vitamins (A & C), potassium, Nordamnacanthal and Morindone, anthraquinones, fitosterols, flavonolglicosides, aucubine, alizarine and others. In the range of therapeutic activities are included: 1) Immune-stimulant: The fruit's extracts stimulate the release of various interleukins, including interleukine-1beta, IL-10, IL-12 and interferon-gamma. 2) Anti-inflammatory effect: The fruit's extracts inhibits tumor necrosis factor-alpha, an important mediator of the inflammation process Proceedings of the 7th Annual Conference (Eicosanoids and other bioactive lipids in cancer, inflammation and related disease 2001, Nashville, Tenn.) publishes Morinda's anti-inflammatory properties—greater than Celecoxib—to selectively inhibit COX2. Its anti-inflammatory activity is also explained by its strong antioxidant properties, scavenging free radicals and diminishing lipid peroxidation. One study compared Noni with three known anti-oxidants: Vitamin C, grape seed powder and picnogenol, offering greater capacity to scavenge free radicals (2.8, 1.1, and 1.4 respectively). *Morinda* provides at least 31 active principles in a single therapeutic.

*Petiveria alliacea* (Anamú, Apacin, Apacina, Apazote De Zorro, Aposin, Ave, Aveterinaryte, Calauchin, Chasser Vermine, Congo Root, Douvant-douvant, Emeruaiuma, Garlic Guinea Henweed, Guine, Guinea, Guinea hen leaf, Gully Root, Herbe Aux Poules, Hierba De Las Gallinitas, Huevo De Gato, Kojo Root, Kuan, Kudjuruk, Lemtewei, Lemuru, Mal Pouri, Mapurit, Mapurite, Mucura-caa, Mucura, Mucuracaa, Ocano, Payche, Pipi, Tipi, Verbena Hedionda, Verveine Puante, Zorrillo) contains Allantoin, Arborinol, Arborinoliso Astilbin, Benzaldehyde, Benzoic-acid Benzyl-2-hydroxy-5-ethyl-trisulfide, Coumarin, Diallyl-disulfide, Dibenzyl Trisulfide, Engeletin, alpha Friedelinol, Isoarborinol, Isoarborinol-acetate, Isoarborinol-cinnamate, Isothiocyanates, Kno3, Leridal, Leridol, Leridol-5-methyl Ether, Lignoceric Acid, Lignoceryl Alcohol, Lignoceryl Lignocerate, Linoleic Acid Myricitrin, Nonadecanoic Acid, Oleic Acid, Palmitic Acid, Pinitol, Polyphenols, Proline, trans-n-methyl-4-methoxy, Senfol, β-Sitosterol, Stearic Acid, Tannins, and Trithiolaniacine. Its therapeutic activities include anti-inflammatory, immune-stimulant and antimicrobial effects. Allyl disulfide, allyl alcohol, and its ester strongly depressed cell proliferation of HIV-1-infected cells.

The allyl alcohol, in particular, completely inhibited cell growth of HIV-1-infected cells, ultimately killing the viable CEM/LAV-1 cells. The results suggest that the effect of the allyl alcohol and its esters resulted in remarkable promotion of the cytopathic effect induced by HIV-1 virus (Shoji S., et al. Allyl compounds selectively killed human immunodeficiency virus (type 1)-infected cells. Biochem Biophys Res Commun. 1993; 194:610-21). Petiveria provides 25 active principles.

*Sutherlandia frutescens* (Cancer Bush, also *Sutherlandia Microphylla*) contains L-canavanine, pinitol, GABA (gamma aminobutyric acid), and asparagine. In addition, a novel triterpenoid glucoside known as 'SU1' has been isolated and characterized. The therapeutic indications include anti-inflammatory, antioxidant, and immuno-modulator. One study showed that Sutherlandia extracts contain inhibitory compounds active against HIV target enzymes, thus showing a potential mechanistic action of this plant in aiding HIV-positive patients (Harnett S M, Oosthuizen V, van de Venter M. Anti-HIV activities of organic and aqueous extracts of *Sutherlandia frutescens* and *Lobostemon trigonus*. J Ethnopharmacol. 2005; 96:113-9). This phytomedicine provide at least 5 active principles.

*Tabebuia avellanedae* (Pau d'arco, *Ipê*, Lapacho, Tahuari, Taheebo, Trumpet Tree, *Tabebuia Ipê*, Tajy; also *T. ipe, T. nicaraguensis, T. schunkeuigoi, T. serratifolia, T. altissima, T. palmeri, T. impetiginosa, T. heptaphylla, Gelseminum avellanedae, Handroanthus avellanedae, H. impetiginosus, Tecoma adenophylla, Tec. avellanedae, Tec. eximia, Tec. impetiginosa, Tec. integra, Tec. ipe*) extracts contain diverse quinone derivatives and a small quantity of benzenoids and flavonoids, including beta-lapachone, xyloidone, tabebuin, quercetin, tecomine, and steroidal saponins. One important ingredient is lapachol, a derivative of which was patented in 1975. It has anti-inflammatory and antibacterial effects. Recent studies on the effect of beta-lapachone, a quinone obtained from the bark of this tree, are shedding new light into the possible molecular mechanism of its activity. Beta-lapachone is a potent and selective inhibitor of HIV-1 LTR-directed gene expression, at concentrations that have minor effects on cells. At these concentrations, beta-lapachone inhibited p24 antigen production in cells either acutely or chronically infected with HIV-1.

Their target is transcriptional function of the LTR (Li C J, Zhang L J, Dezube B J. Three inhibitors of type 1 human immunodeficiency virus long terminal repeat-directed gene expression and virus replication. Proc Natl Acad Sci USA. 1993; 90:1839-42). The incorporation of Tabebuia provides at least 32 active principles in a single therapeutic.

*Uncaria tomentosa* (Cat's Claw, Peruvian Cat's Claw, Samento, Saventaro, Uña de Gato, also *Uncaria guianensis*) has several alkaloids including pentacyclic oxindol alkaloids (POA) (isomitraphylline, isopteropodine, mitraphylline, pteropodine, speciophylline, uncarine F), tetracyclic oxindol alkaloids (TOA) (isorynchophylline, rynchophylline), glycosides (triterpenic quinovic acid glycosides), hirsutine, tannins, catechins, phytosterols (beta-sitosterol, campesterol, stigmasterol), triterpenes, polyphenols, flavanols and oligomeric proanthocyanidins (OPC). It is an immune-stimulant, an anti-inflammatory, and antioxidant. A standardized extract of uncaria tomentosa has been successfully used for the past six years in clinical studies, either as an isolated treatment or in conjunction with AZT to treat HIV positive and AIDS patients. It has been found to impede the multiplication of the HIV virus, to activate the immune system and to stop the development of cancerous cells. Three groups were studied. The first group was HIV positive and treated for five years. The disease was prevented from progressing in almost all patients. The second group exhibited the first sign of AIDS and was treated for six years. In almost all patients the abnormal blood values were improved within one year and the patients lost the symptoms of clinical illness. "This good condition has been maintained to this day." The third group has been treated for one year with Uncaria tomentosa and AZT. Abnormal blood values were improved, clinical symptoms were lessened and the secondary infections of AZT were prevented in almost all patients. (Keplinger, U. M., "Einfluss von Krallendom extract auf Retrovirale Infektioned", Zurcher AIDS Kongress, Zurich Switzerland, 16-17 Oct. 1992, program and abstracts). Uncaria provides at least 29 active principles.

*Vitex agnus castus* (Chaste Tree or chaste berry) The most important active principles are an essential oil, two iridoid glycosides (aucubine and agnuside); a flavone (casticin, which seems to be the primary active principle) and 3 minor flavonoids derived from kaempferol and quercetin. A recent study has shown G2-M arrest and antimitotic activity mediated by casticin.

Organizational Improvers.—

Fulvic Acid (FA) Deals with a mixture of low molecular weight components among which are uronic acid, glucosides and amino acids. The biologic activity of fulvic acid is uniquely determined by the functional groups of its molecules (carboxyls, hydroxiphenyls, hydro-quinone, amino and imido groups). Fulvic acid (FA) is resistant to microbial degradation. Fulvic acid accelerates oxidative phosphorylation and protein synthesis. Antitumoral and anti-oxidative effects: FA protects the cellular membrane of the action of free radicals and heavy metals. It can scavenge and eliminate free radicals because of its weak acid properties. It can combine with heavy metals and body toxins, removing them form the system. It increases the activity of enzymatic antioxidant systems such as superoxide dismutase. Anti-inflammatory: FA is a powerful anti-inflammatory; reduces edema by 77%, minimizing pain. Its anti-oxidative properties also help prevent inflammation. FA increases the citotoxic activity of macrophages as well as the synthesis of Interferon and other cytokines. Fulvic acid increases the phagocytic activity of macrophages, the mechanism being similar to that produced by IL-4.

*Hydrocotile asiatica* (Gotu Kola, Bramhi, Pennywort, Marsh Penny, Pennywort and *Centella asiatica*) contains terpenoids (asiaticoside, brahmoside and brahminoside), aglycones (saponin glycosides), asiaticentoic acid, centellic acid, centoic acid and madecassic acid, sesquiterpenes (caryophyllene, trans-B-farnesene), volatile oils (Germacrene D), alkaloids (hydrocotylin), flavonoids (Quercetin, kaempferol), phytosterols (stigmasterol and sitosterol), and vallerine, fatty acids, resin, and tannins. These active principles confer anti-inflammatory and immunemodulating properties. *Centella asiatica* is a medicinal plant traditionally used to treat a variety of disorders including inflammatory conditions and infections. Nitric oxide (NO) produced from activated macrophages plays a role in both inflammatory and anti-inflammatory processes. This study examined whether *Centella asiatica* (CA) modulates the production of NO and tumor necrosis factor-alpha (TNF-alpha) by J774.2 mouse macrophages. CA increased NO production; an increase also occurred when CA was administered with lipopolysaccharide (LPS), a known macrophage activator. TNF-alpha secretion was correlated with NO production and increases were associated with an elevation in TNF-alpha mRNA. The only effect on iNOS gene expression was an inhibition with the CA ethanol extract in the presence of LPS, consistent with the reduction in NO under these conditions. These studies show that CA extracts can either increase or decrease NO production by macrophages and that these effects are predominantly mediated through an effect on TNF-alpha expression. (Punturee K., et al. Thai medicinal plants modulate nitric oxide and tumor necrosis factor-alpha in J774.2 mouse macrophages. J Ethnopharmacol. 2004; 95:183-9). CA provides 59 active principles.

*Opuntia ficus indica* (Indian Fig, Nopal, Cactus pear, prickly pear) fruit contains vitamin C and characteristic betalain pigments, which radical-scavenging properties and anti-oxidant activities have been shown in vitro. It also contains vitamins (A, B1, B2, B3,) carothenoids, betaxanthins, tannins, 17 amino acids (of which 7 are essential) and minerals. From the stems and fruits of prickly pear cactus, eight flavonoids, kaempferol, quercetin, kaempferol 3-methyl ether, quercetin 3-methyl ether, narcissin, (+)-dihydrokaempferol (aromadendrin, (+)-dihydroquercetin (taxifolin), eriodictyol, and two terpenoids have been identified. Several studies have demonstrated that Opuntia produces a chemical substance which accelerates the synthesis of Heat Shock Proteins (HSP) in response to aggressor agent's impacts, while at the same time they reduce the consumption of these proteins. Thus they improve the protective, reparative and recuperative cellular mechanisms, increasing cell survival and minimizing organ and tissular damage. This is particularly important in AIDS patients. HSP proteins also participate in the immune responses, acting as macrophage and other immune-competent cells inductors which participate in the innate immune mechanisms, thus contributing to the immunological system. This phytomedicine incorporates at least 80 active principles in a single therapeutic.

Shark cartilage This natural compound contains Chondroitin sulfate. The results of one controlled trial showed that CD4(+)/CD8(+) ratio increased in patients that received shark chondroitin. The results of this study suggest that shark chondroitin could enhance immune function in HIV patients. (Xu Y J, et al. [Effect of Shark Chondroitin on T Lymphocyte Subsets of Cancer Patients. Zhongguo Shi Yan Xue Ye Xue Za Zhi. 2001; 9:95-96). Chondroitin sulfate, a fusion inhibitor, appears to work by blocking the ability of HIV, to infect a cell (Konlee M. Sulfated polysaccharides (chondroitin sulfate and carrageenan) plus glucosamine sulfate are potent inhibitors of HIV. Posit Health News. 1998; 4-7).

EXAMPLE 2

Composition—HIV/AIDS and Immune Disorders

A particularly preferred composition is shown in Table 1. Ratios reflect concentration of active ingredient over the natural state. Amounts provided are mg of extract. Obviously, the amount should be increased where the strength is reduced, and vice versa.

TABLE 1

Herbaria

| Active Agent | Ratio | Amount (mg) |
|---|---|---|
| Energy enhancers | | |
| Eleutherococcus senticosus root extract | 5:1 | 20 |
| Panax ginseng root extract | 5:1 | 13 |
| Panax quinquefolius | 4:1 | 17 |
| Pfaffia paniculata root extract | 4:1 | 34 |
| Rhodiola rosea root extract | 5:1 | 7 |
| Schizandra chinensis | 5:1 | 7 |
| Bio-Intelligence modulators | | |
| Andrographis paniculata | 5:1 | 34 |
| Astragalus membranaceus root extract | 5:1 | 34 |
| Coriolus versicolor | 10:1 | 54 |
| Echinacea angustifolia root | 6:1 | 13 |
| Echinacea purpurea root | 6:1 | 13 |
| Ganoderma lucidum mushroom extract | 10:1 | 40 |
| Grifola frondosa mushroom extract | 10:1 | 20 |
| Hydrastis canadensis root extract | 5:1 | 13 |
| Lentinus edodes | 4:1 | 40 |
| Morinda citrifolia | 5:1 | 13 |
| Petiveria alliacea | 1:1 | 34 |
| Sutherlandia frutescens extract | 1:1 | 67 |
| Tabebuia avellanedae | 4:1 | 40 |
| Uncaria tomentosa | 4:1 | 40 |
| Vitex agnus castus | 5:1 | 17 |
| Organization improvers | | |
| Fulvic acid | 3:4 | 13 |
| Hydrocotile asiatica | 5:1 | 20 |
| Opuntia ficus indica | 5:1 | 7 |
| Shark cartilage | 4:1 | 40 |
| Total | | 637 |

EXAMPLE 3

A Clinical Study of Formulation's Effectiveness and Tolerance

A study was undertaken under my direction to evaluate the effects of the therapeutic formula object of this patent—and formulated under the precepts herein included—in eleven HIV-infected adult patients. The effects of the composition, a combination of phytomedicines formulated under the precepts of the Systemic Medicine, were evaluated in a prospective study in which 11 HIV-infected adults received (kaletra+ combivir) or (viracept+combivir) during 6 months, without improvement. After that time, the formulation (10 capsules twice daily) was added to the treatment. The duration of this treatment was 16 weeks. Study participants were: male 9 (81.8%), and Hispanic (100%). The median age was 46.5 years. The median pretreatment with CD4 cell count was 184 cells/mm3, and median plasma HIV-1 RNA was 18.586 copies/mL. After 16 weeks of combined therapy, the median CD4 increased from baseline to 250 cells/mm3, which corresponds to a 35.86% increase. The proportion of patients with plasma HIV-1 RNA<50 copies/mL after 16 weeks of treatment was 85.71%. The results of this study demonstrate that the combination is better than those obtained with a treatment based solely on anti-retrovirals. None of the patients discontinued treatment due to adverse reactions. This combination improved clinical symptoms and quality of life in 94.59% of the patients. The results of this study confirm the effectiveness' of the combination of antiretrovirals plus the composition object of this patent in the management of AIDS patients. Preliminary results on this population strongly suggest that this therapy may offer unexpectedly superior comparative benefits to HIV—infected patients—when contrasted to traditional therapies.

EXAMPLE 4

Principles for Selecting Synergistic Combinations

In order to expand the range of formulations encompassed by the invention, we have categorized beneficial plants into one of three groups, each of which should be present for synergistic effect. The classifications are Energy, Bio-Intelligence and Organization. Plants classified under Energy are associated with ATP synthesis (such as the Krebs cycle, oxidative phosphorylation, beta-oxidation, etc.). Plants classified under Bio-Intelligence are those that regulate the neuroendocrine and immunological systems and cellular processes, thus controlling the interactions between the various systems in the body. Finally, plants classified under Organization are those that relate to the structure and function of specific organs.

Combinations of plants from these three classification groups have synergistic effect because they address each necessary component for total health—in effect they provide the triangle on which healing is fully supported.

An illustrative example of synergy in medicinal plants is an in vitro study that demonstrates how the activity of herbal Berberine alkaloids is strongly potentiated by the action of 5'-methoxyhydnocarpin (5'-MHC)—an active principle of another phytomedicine (denominated Hydnocarpus wightiana). It shows a strong increase of accumulation of berberine in the cells in the presence of 5'-MHC, indicating that this plant compound effectively disabled the bacterial resistance mechanism against the berberine antimicrobial, thus showing the synergy of both substances. Stermitz F R, et al., Synergy in a medicinal plant: antimicrobial action of berberine potentiated by 5'-methoxyhydnocarpin, a multidrug pump inhibitor. Proc Natl Acad Sci USA. 2000; 97:1433-7.

It may further be demonstrated synergistic effect on a molecular scale by studying the gene expression profile changes in response to various plant ingredients and combinations thereof. Experiments are already underway demonstrating the expression profile in response to the formulations. We will be aided in this work because researchers have already begun studying the expression profiles of various medicinal plants, thus providing a database of knowledge from which to build. E.g., Liu L, et al., Effects of Si-Jun-Zi decoction polysaccharides on cell migration and gene expression in wounded rat intestinal epithelial cells. 2005; 93:21-9; and Gohil, et al., mRNA Expression Profile of a Human Cancer Cell Line in Response to *Ginkgo Biloba* Extract: Induction de Antioxidant Response and the Golgi System, Free Radic Res. 2001; 33:831-849.

It may also be possible to add tests of plants' combinations for further demonstration of synergistic effects by using experimental models.

It may further be added a gene expression study using micro-array technology to demonstrate modulation of genes involved in HIV/AIDS and/or Immune disorders with the use of this composition.

What is claimed is:

1. A phyto-nutraceutical composition comprising: 34 mg of *Andrographis paniculata*, 34 mg of *Astragalus membranaceus*, 54 mg of *Coriolus versicolor*, 13 mg of *Echinacea angustifolia*, 13 mg of *Echinacea purpurca*, 20 mg of *Eleutherococcus senticosus*, 13 mg of Fulvic acid, 40 mg of *Ganoderma lucidum*, 20 mg of *Grifola frondosa*, 13 mg of *Hydrastis canadensis*, 20 mg of *Hydrocotile asiatica*, 40 mg of *Lentinus edodes*, 13 mg of *Morinda citrifolia*, 7 mg of *Opuntia ficus indica*, 13 mg of *Panax ginseng*, 17 mg of *Panax quinquefolius*, 34 mg of *Petiveria alliacea*, 34 mg of *Pfaffia paniculata*, 7 mg of *Rhodiola rosea*, 40 mg of Shark cartilage, 7 mg of *Schizandra chinensis*, 67 mg of *Sutherlandia frutescens*, 40 mg of *Tabebuia avellanedae*, 40 mg of *Uncaria tomentosa* and 17 mg of *Vitex agnus castus* together with pharmaceutically acceptable excipients.

* * * * *